(12) United States Patent
Rajasekharan et al.

(10) Patent No.: US 12,416,598 B2
(45) Date of Patent: Sep. 16, 2025

(54) DERIVED ALKALINITY

(71) Applicant: Hach Company, Loveland, CO (US)

(72) Inventors: Vishnu Vardhanan Rajasekharan, Fort Collins, CO (US); Cary Burton Jackson, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 580 days.

(21) Appl. No.: 17/709,684

(22) Filed: Mar. 31, 2022

(65) Prior Publication Data
US 2022/0317080 A1    Oct. 6, 2022

Related U.S. Application Data

(60) Provisional application No. 63/168,569, filed on Mar. 31, 2021.

(51) Int. Cl.
*G01N 27/27*    (2006.01)
*G01N 27/30*    (2006.01)
(Continued)

(52) U.S. Cl.
CPC ........... *G01N 27/27* (2013.01); *G01N 27/302* (2013.01); *G01N 27/308* (2013.01);
(Continued)

(58) Field of Classification Search
CPC .... G01N 27/27; G01N 27/302; G01N 27/308; G01N 27/44; G01N 31/005; G01N 31/22; G01N 31/182; G01N 31/1846
See application file for complete search history.

(56) References Cited

U.S. PATENT DOCUMENTS 5,435,969 A  *  7/1995  Hoots ................. G01N 33/18
                                                    422/18
8,349,614 B2   1/2013  Hintz et al.
(Continued)

FOREIGN PATENT DOCUMENTS

KR       20210017795 A  *  2/2021

OTHER PUBLICATIONS

Chon et al., English translation of KR20210017795A, , 2021 (Year: 2021).*

*Primary Examiner* — Luan V Van
*Assistant Examiner* — Shizhi Qian
(74) *Attorney, Agent, or Firm* — Ference & Associates LLC

(57) ABSTRACT

An embodiment provides a method for deriving an alkalinity measurement, including: introducing a fluid sample; measuring, a phosphate amount of the fluid sample using a colorimetric reagent; measuring a pH of the fluid sample, wherein the pH of the fluid sample correlates to a hydroxide amount of the fluid sample; introducing an acid to convert all the inorganic carbon to carbon dioxide; applying a positive potential to the SP3 substituted carbon electrode; introducing, prior to or substantially simultaneously during the application of the positive potential to the SP3 substituted carbon electrode and in the reaction chamber, at least one acid reagent comprising a metallic catalyst that converts the carbonate and the partially oxidized species to carbon dioxide; determining total organic carbon by detecting an amount of carbon dioxide produced by the oxidation; determining the total organic carbon from the oxidation of the organic carbon species, and determining a derived alkalinity based upon the phosphate amount, the hydroxide amount, and the amount of carbon dioxide generated from the inorganic carbon. Other aspects are described and claimed.

10 Claims, 5 Drawing Sheets

(51) Int. Cl.
*G01N 31/00* (2006.01)
*G01N 31/22* (2006.01)
*G01N 33/18* (2006.01)

(52) U.S. Cl.
CPC .......... *G01N 31/005* (2013.01); *G01N 31/22* (2013.01); *G01N 33/182* (2013.01); *G01N 33/1846* (2013.01)

(56) References Cited

U.S. PATENT DOCUMENTS

| | | | | |
|---|---|---|---|---|
| 2007/0254374 | A1* | 11/2007 | Iharada | G01N 33/1846 |
| | | | | 436/146 |
| 2009/0308745 | A1* | 12/2009 | McLeod | C02F 9/00 |
| | | | | 204/405 |
| 2015/0129435 | A1* | 5/2015 | Franaszczuk | G01N 27/49 |
| | | | | 205/785.5 |
| 2018/0224397 | A1* | 8/2018 | Kroll | G01N 27/302 |
| 2019/0033249 | A1* | 1/2019 | O'Mahony | G01N 33/1846 |
| 2019/0317044 | A1* | 10/2019 | Rajasekharan | G01N 27/4167 |
| 2019/0352200 | A1* | 11/2019 | Jolly | C02F 1/72 |
| 2022/0298034 | A1* | 9/2022 | McLeod | C02F 1/66 |

* cited by examiner

DERIVED ALKALINITY

CROSS REFERENCE TO RELATED APPLICATION

This application claims priority to U.S. Provisional Patent Application Ser. No. 63/168,569, filed on Mar. 31, 2021, and entitled "DERIVED ALKALINITY," the contents of which are incorporated by reference herein.

BACKGROUND

This application relates generally to determining an alkalinity in aqueous samples and, more particularly, to the measurement of the alkalinity using measurements of phosphate, hydroxide, carbon dioxide, and oxidized species of said samples.

Ensuring water purity is critical in many applications, for example in municipalities that provide drinking water and in numerous other industries such as pharmaceuticals, chemicals and other manufacturing fields. A proper pH and alkalinity measurement of a sample may be required for the treatment of the water. Additionally, the presence of organic compounds in the water may suggest a failure in filtration and/or other components and systems that, if left unchecked, can damage expensive industrial systems, impact product quality, be detrimental to public health, and even affect profit margins. As an example, drinking water quality may require treatment with disinfection reagents. A quantity of disinfection reagents is dependent on an accurate measurement of alkalinity and total organic carbon to prevent overuse of reagents leading to disinfection by-products.

BRIEF SUMMARY

In summary, one embodiment provides a method for deriving an alkalinity measurement, comprising: introducing, in a reaction chamber of an analyzer, a fluid sample comprising inorganic carbon, wherein the reaction chamber includes an electrochemical cell and wherein the electrochemical cell comprises an SP3 substituted solid carbon electrode doped with a conductivity elevating composition; measuring, using a phosphate analyzer of the analyzer, a phosphate amount of the fluid sample using a colorimetric reagent; measuring, using a pH sensor of the analyzer, a pH of the fluid sample, wherein the pH of the fluid sample correlates to a hydroxide amount of the fluid sample; introducing an acid reagent to convert the inorganic carbon to carbon dioxide, wherein the inorganic carbon comprises carbonate and bicarbonate; applying, using a generator of the analyzer, a positive potential to the SP3 substituted carbon electrode, the positive potential being sufficient to oxidize organics in the fluid sample to produce carbonate and partially oxidized organics; introducing, prior to or substantially simultaneously during the application of the positive potential to the SP3 substituted carbon electrode and in the reaction chamber, at least one acid reagent comprising a metallic catalyst that converts the carbonate and the partially oxidized species to carbon dioxide; determining total organic carbon by detecting, using at least one detector of the analyzer, an amount of carbon dioxide produced by the oxidation; and determining a derived alkalinity based upon the phosphate amount, the hydroxide amount, and the amount of carbon dioxide generated from the inorganic carbon.

Another embodiment provides a device for deriving an alkalinity measurement, comprising: a housing comprising: a reaction chamber, wherein the reaction chamber includes an electrochemical cell and wherein the electrochemical cell comprises a SP3 substituted carbon electrode doped with a conductivity elevating composition; at least one detector; a phosphate analyzer; a pH sensor; and a generator; the device for deriving an alkalinity measurement being configured to: receive, in the reaction chamber of an analyzer, a fluid sample comprising inorganic carbon; measure, using the phosphate analyzer of the analyzer, a phosphate amount of the fluid sample using a colorimetric reagent; measure, using the pH sensor of the analyzer, a pH of the fluid sample, wherein the pH of the fluid sample correlates to a hydroxide amount of the fluid sample; introducing an acid reagent to convert the inorganic carbon to carbon dioxide, wherein the inorganic carbon comprises carbonate and bicarbonate; apply, using the generator of the analyzer, a positive potential to the SP3 substituted carbon electrode, the positive potential being sufficient to oxidize organics in the fluid sample to produce carbonate and partially oxidized organics; introduce, in the reaction chamber prior to or substantially simultaneously during application of the positive potential to the SP3 substituted carbon electrode, at least one acid reagent comprising a metallic catalyst that converts the carbonate and the partially oxidized organics to carbon dioxide; determine total organic carbon by detecting, using at least one detector of the analyzer, an amount of carbon dioxide produced by the oxidation; and determining a derived alkalinity based upon the phosphate amount, the hydroxide amount, and the amount of carbon dioxide generated from the inorganic carbon.

A further embodiment provides A product for measuring alkalinity in a sample, comprising: a storage device that stores code, the code being executable by a processor and comprising: code that introduces, in a reaction chamber of an analyzer, a fluid sample comprising inorganic carbon, wherein the reaction chamber includes an electrochemical cell and wherein the electrochemical cell comprises an SP3 substituted solid carbon electrode doped with a conductivity elevating composition; code that measures, using a phosphate analyzer of the analyzer, a phosphate amount of the fluid sample using a colorimetric reagent; code that measures, using a pH sensor of the analyzer, a pH of the fluid sample, wherein the pH of the fluid sample correlates to a hydroxide amount of the fluid sample; code that introduces an acid reagent to convert the inorganic carbon to carbon dioxide, wherein the inorganic carbon comprises carbonate and bicarbonate; code that applies, using a generator of the analyzer, a positive potential to the SP3 substituted carbon electrode, the positive potential being sufficient to oxidize organics in the fluid sample to produce carbonate and partially oxidized organics; code that introduces, prior to or substantially simultaneously during the application of the positive potential to the SP3 substituted carbon electrode and in the reaction chamber, at least one acid reagent comprising a metallic catalyst that converts the carbonate and the partially oxidized species to carbon dioxide; code that determines total organic carbon by detecting, using at least one detector of the analyzer, an amount of carbon dioxide produced by the oxidation; and code that determines a derived alkalinity based upon the phosphate amount, the hydroxide amount, and the amount of carbon dioxide generated from the inorganic carbon.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
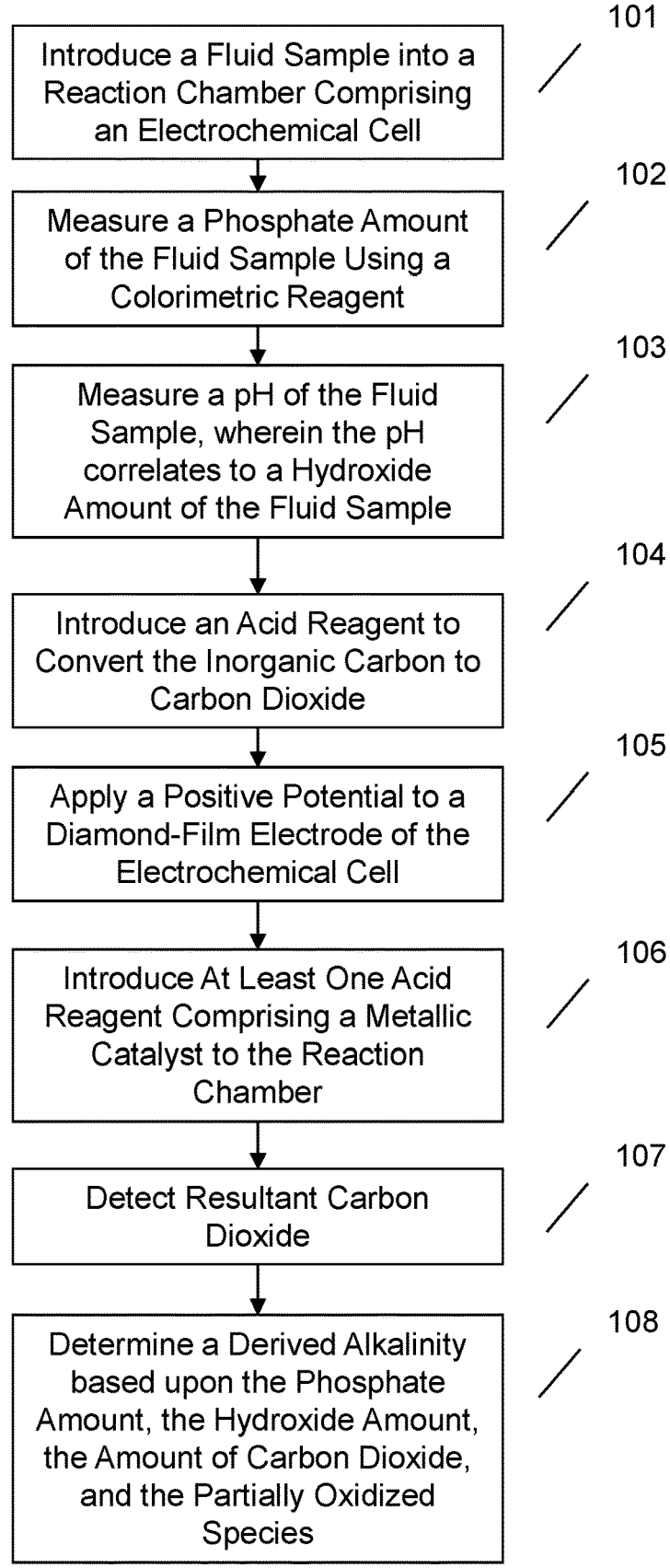
FIG. 1 illustrates an example method of deriving alkalinity in a fluid sample.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional alkalinity measurements may have some limitations. Alkalinity is the buffering capacity of an aqueous sample. Alkalinity is an important parameter that is measured in source, distribution, industrial and municipal process water matrices. In conventional methods, a strong acid may be added into the sample solution incrementally for titrating. The endpoint may be a pH 8.3 or pH 4.5 for Phenolphthalein and Total Alkalinity respectively. The titration presents safety hazards due to the handling, presence, and storage of strong acids. Additionally, conventional instruments may have performance and maintenance concerns.

Additionally, harmful disinfection byproducts (DBP) may be formed due the reaction between organic precursors found in water sources and disinfectants added to kill microorganisms. One of the uses of the measurement of alkalinity is reducing the concentration of organic precursors that are present in the form of total organic carbon (TOC). This is achieved by precipitation of the organic precursors like humic acids.

For example, these organic precursors are responsible for the formation of harmful disinfection by-products (DBP) in water matrices in the presence of disinfectants like chlorine. Simultaneous measurement of alkalinity and organics as TOC will support reduction of TOC and subsequent reduction of the formation of DBP according to regulations. Additionally, the method described here allows for raw water TOC and alkalinity samples to be taken at the same location.

A variety of total organic carbon (TOC) methods and techniques exist today. However, many of the existing techniques require the use of hazardous reagents (e.g., strong acids and oxidizing agents, etc.) and are required to be performed in harsh environments (e.g., under ultraviolet light, in high temperature ovens, etc.) in order for the oxidation reactions to be properly executed. These issues have led to the development of safer and more cost-effective electrochemical devices that are capable of oxidizing organic carbon and determining TOC levels in aqueous solutions.

One such device, a TOC analyzer produced and distributed by O.I. Analytical, College Station, Texas (i.e., the 9210e On-line TOC Analyzer), utilizes a thin diamond-film electrode doped with boron to carry out the oxidation of the organic material to produce carbon dioxide (e.g., by generating hydroxyl radicals and ozone on the surface of the boron doped diamond (BDD) electrode). The use of boron serves as a better electrode material than carbon-based or other metallic materials (e.g., silver, gold, mercury, nickel, etc.) because these materials poorly oxidize and may eventually themselves become oxidized. The O.I. TOC analyzer comprises one or more sensors capable of detecting carbon dioxide produced by the boron doped diamond electrode. In an embodiment, a thick film SP3 substituted carbon region may be used, the advantages of which are described by U.S. Pat. No. 10,724,984, titled SP3 SUBSTITUTED CARBON ELECTRODE TOC ANALYSIS USING METALLIC CATALYST, and filed Jul. 29, 2017 the contents of which are incorporated by reference in their entirety.

However, existing TOC analyzers utilizing BDD electrodes may fall short of measuring all of the oxidized carbon species. More particularly, hydroxyl radical oxidation of carbon species can produce two oxidation products, carbonate and oxalate, the proportion of which depends generally on the number of carbon atoms in the molecule (e.g., C1 (methanol) can only form carbonate (100%), C2 (ethanol) forms carbonate (~67%) and oxalate (~33%), etc.). Carbonate is measured in a $CO_2$ gas analyzer by acid addition that converts the carbonate into $CO_2$ gas. However, it is unclear whether current BDD TOC methods are able to completely measure the oxalate proportion, which may therefore result in an incomplete measurement (i.e., an underestimation of the total TOC content). Additionally, the lifespan of the thin film electrode is short because the thin film coating on the electrode suffers from delamination.

Advances in research have led to the discovery that adding a manganese catalyst, or other metallic catalyst, to a sample enables the oxalate to be converted to $CO_2$ gas, which can then be measured. However, these conventional methods still require the use of ozone to generate the active ingredient (i.e., the hydroxyl radical), which requires an expensive ozone generator. Additionally, the gas required for this technique is oxygen, which requires an oxygen concentrator in the analysis system.

Conventional instruments and methods cannot determine both alkalinity and organics simultaneously at the same location. This limitation of simultaneous measurement limits control of the mount of chemicals added to a system. For example, too high of a level of sodium bicarbonate may be added to reduce TOC. Without simultaneous monitoring, DBP levels may be exceed regulatory or institutional limits.

Accordingly, an embodiment provides a method and system for determining alkalinity and TOC simultaneously. In an embodiment, real time controls may optimize chemical addition. The optimized chemical levels may remove organic precursors. The optimized chemical levels may reduce DBP formation. The optimization may be used for a variety of source water compositions. an embodiment provides a method for oxidizing organic carbon in an aqueous solution and measuring the total organic carbon resulting from the oxidation process in combination with determining a derived alkalinity of the fluid sample. In an embodiment, a fluid sample comprising organic carbon is introduced into a reaction chamber of a total organic carbon analyzer. The reaction chamber may comprise an electrochemical cell with a SP3 substituted carbon electrode doped with a conductivity elevating composition (e.g., boron, etc.). In an embodiment, an amount of phosphate of the fluid sample may be measured using colorimetric methods. In an embodiment, a pH of the fluid sample may be measured or determined to determine a hydroxide amount of the fluid sample. An embodiment may then apply a positive potential to the electrode to oxide any organics in the fluid sample to their corresponding oxidation process. An embodiment may introduce a metallic catalyst (e.g., manganese, iron, nickel, chromium, another transition metal capable of oxidizing the organics in the fluid sample, etc.) to the fluid sample. These metallic catalysts will be oxidized to higher valent Mn (VII). These higher valent manganese species assist in the conversion of intermediate partially oxidized species (e.g., oxalate, etc.) to carbon dioxide which can then be detected and/or measured by at least one carbon dioxide detector/sensor. In this process Mn (VII) converts back to Mn(II). Such a method ensures complete recovery of all oxidized carbon species. The system and method may derive an alkalinity to reduce treatment chemical and reduced the formation of disinfection by-products.

The illustrated example embodiments will be best understood by reference to the figures. The following description is intended only by way of example, and simply illustrates certain example embodiments.

Referring now to FIG. 1, an embodiment may measure the total organic carbon content present in an aqueous sample. At 101, an aqueous fluid sample containing organic carbon (e.g., water from a source, a solution containing a dissolved specimen, etc.) may be introduced into a TOC and alkalinity analyzer. In an embodiment, the TOC analyzer comprises an appropriate housing that is sealed to create a closed system in which carbon dioxide generated through an oxidation process cannot escape from the system prior to detection. In an embodiment, the housing comprises a reaction chamber that is configured to contain the aqueous fluid sample. The housing may also include a head space that may be configured to capture the gas-phase carbon dioxide. In an embodiment, the analyzer may be a stopped-flow design. A stopped-flow design may be configured to capture a fluid sample and perform steps upon a volume not continuously flowing through the analyzer.

In an embodiment, the reaction chamber may include an electrochemical cell. The electrochemical cell may comprise a plurality of electrodes (e.g., working electrode, reference electrode, counter electrode, etc.) in which the working electrode may be an SP3 substituted solid carbon electrode capable of oxidizing organics in an aqueous sample to produce carbon dioxide. In an embodiment, the SP3 substituted solid carbon electrode may be doped with a conductivity inducing material (e.g., boron, etc.) that is capable of raising the conductive band of the SP3 substituted solid carbon electrode. For simplicity purposes, the majority of the discussion herein will refer to boron as the conductivity inducing material, however, it should be understood that other suitable atoms capable of raising the conductive band of the SP3 substituted solid carbon electrode may also be used. In an embodiment, the electrode may be immersed in and be in contact with the sample aqueous fluid sample.

At 102, in an embodiment an amount of phosphate in the fluid sample may be measured. The phosphate measurement may be performed using a colorimetric method. For example, a colorimetric reagent may be combined with at least a portion of the fluid sample. The phosphate of the fluid sample and the colorimetric reagent may form a chromogenic complex. The complex may give an absorption band at a particular wavelength given the colorimetric reagent used. The colorimetric measurement may be measured using a spectrophotometer or the like.

At 103, in an embodiment a pH of the fluid sample may be measured. The pH sensor may be a specialized carbon electrode, standard glass pH electrode, or the like. The pH of the sample may be used to determine an amount of hydroxide in the fluid sample. In an embodiment, the pH sensor and associated circuitry may be an add on or component added to an existing TOC analyzer or device. In other words, the pH measurement may be a retrofit component to a facility with an existing TOC measurement device. In an embodiment, the retrofit may include components to perform feed forward and feedback regulation of water treatment using influent and effluent measurements as discussed herein.

At 104, in an embodiment, an acid reagent may be introduced to convert the inorganic carbon to carbon dioxide in the fluid sample. In an embodiment, the inorganic carbon may contain carbonate and/or bicarbonate. The inorganic carbon that is present in the sample as carbonate and bicarbonates before the oxidation is sparged into NDIR cell in the form of a carbon dioxide. This inorganic carbon in the form of carbon dioxide alone with the hydroxide amount and phosphate amount is used to determine the derived alkalinity. The sparging and generation of carbon dioxide from the inorganic carbon can be facilitated by the acid injection (See FIG. 4).

At 105, in an embodiment, a positive potential may be applied to the SP3 substituted solid carbon electrode. The potential may be applied using an electrical generator or other electrical power producing source (e.g., an external battery, etc.) to produce carbon dioxide at the surface of the SP3 substituted solid carbon electrode. In an embodiment the positive potential may be a potential large enough to sufficiently oxidize the organic compounds in the fluid sample to the oxidation products of carbonate and oxalate. For example, the electrical potential may be from 0.5-20 volts. In an embodiment, a galvanostat may be utilized to keep the current through the electrochemical cell constant.

In an embodiment, the oxidation process using the BDD electrode may comprise the production of hydroxyl radicals by a one electron, one proton process in acidic/neutral media. The efficiency of the production of hydroxyl radical is dependent on the pH of the sample solution. More particularly, above pH 9 there is very little to no production of hydroxyl radicals. As such, in an embodiment, the pH may be maintained at ~1 to produce hydroxyl radicals electrochemically using one or more solid free standing SP3 substituted solid carbon electrodes. Thin film BDDs may undergo thermal stress because of the different thermal expansion coefficients between the substrate and BDD, which limits the current density that can be applied to these substrates. Thick SP3 substituted solid carbon electrode does not have the substrate and therefore the structural and electrical integrity may be maintained at a higher current. Such an embodiment may eliminate the need for adding alkaline solution and ozone, as is required in conventional methods. Additionally, the lack of substrate in the thick-solid free standing SP3 substituted solid carbon electrode eliminates the problem of delamination that occurs on the thin-filmed BDD.

At 106, in an embodiment, at least one acid reagent comprising a metallic catalyst may be introduced into the sample in the reaction chamber. In an embodiment, the at least one acid reagent may react with any carbonate in the sample to produce carbon dioxide gas. In an embodiment, the same or different acid reagent may comprise a manganese (e.g., Mn (II)) catalyst. In an embodiment, regarding the Mn (II) catalyst, the pH of the sample solution may be maintained at acidic levels to oxidize the oxalate into carbon dioxide. The addition of the catalyst effectively ensures complete oxidation of the oxidation products to carbon dioxide. In an embodiment, the fluid sample may be sparged. The sparging may be performed with an inert gas. The inert gas may be nitrogen. Additionally, the fluid sample may be heated. In an embodiment, the method may measure an initial pH of the fluid sample and purging the fluid sample with an inert gas directly thereafter.

At 107, in an embodiment, the carbon dioxide produced by the oxidation process may be measured. In an embodiment, the carbon dioxide may bubble into a collection chamber (e.g., the head space, etc.) where it can be measured using one or more sensors. In an embodiment, the head space may include a gas-phase detector (e.g., a carbon dioxide sensor, etc.) capable of measuring the amount of gas-phase carbon dioxide in the head space. In another embodiment, a liquid-phase detector (e.g., capable of measuring levels of dissolved carbon dioxide in the aqueous-phase, etc.) may be used in lieu of or in combination with the gas-phase detector to attain a complete measurement of the TOC in the sample. In an embodiment, the measured carbon dioxide may be substantially proportional to the amount of organic carbon present in the aqueous sample.

Figure 2:
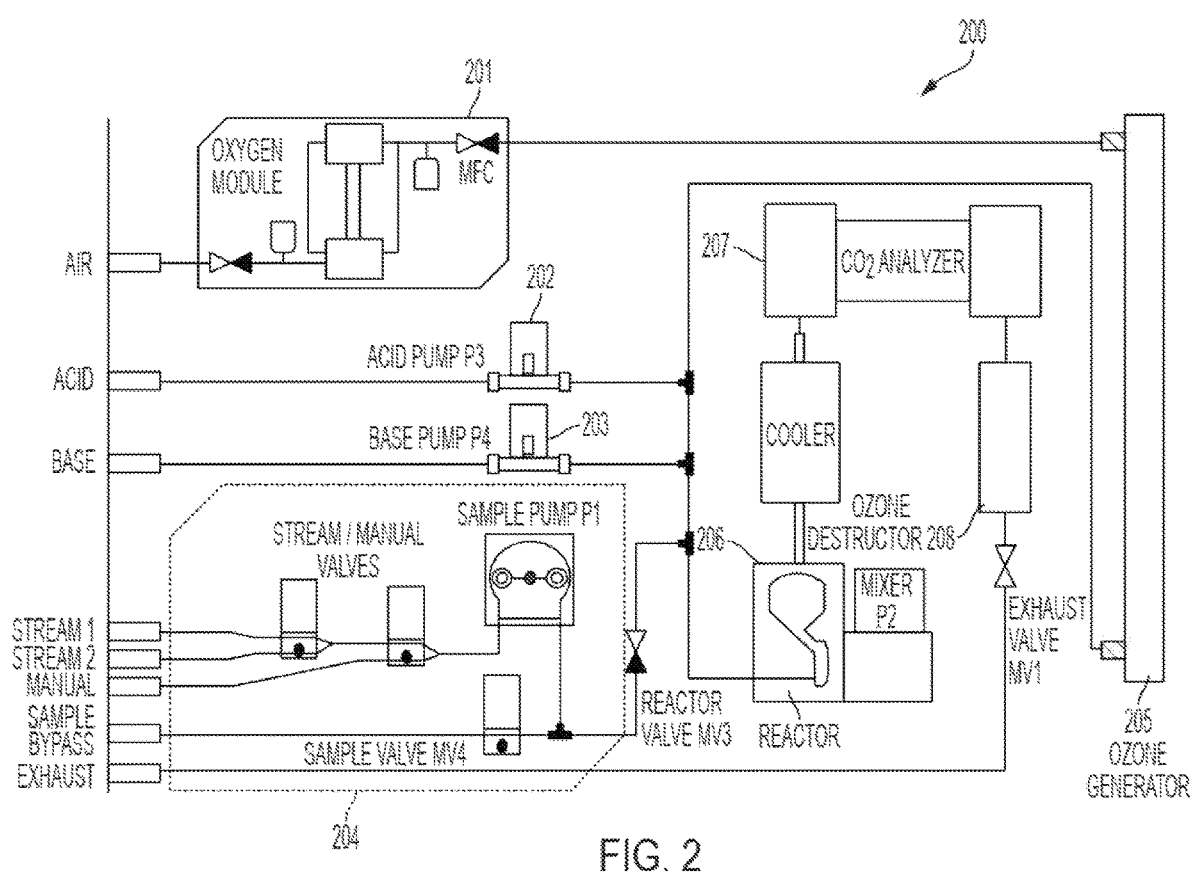
FIG. 2 illustrates a conventional TOC analyzer system.

FIG. 2 illustrates an example conventional analyzer system 200. The conventional system includes an oxygen module 201 which produces the sparge gas by using an oxygen concentrator to concentrate the oxygen from the air. The conventional system includes two reagent introduction mechanisms 202 and 203 which introduce an acid and base, respectively. The sample is introduced into the system using the sample electronics 204. The conventional system also includes an ozone generator 205 which produces ozone to be used in the reactor. The reagents, sample, and ozone are sent to the reactor 206 which mixes the sample. The reactor causes the production of the carbon which can then be measured with the $CO_2$ analyzer 207. The exhaust from the $CO_2$ analyzer 207 is then sent through an ozone destructor 208 before being exhausted.

Figure 3:
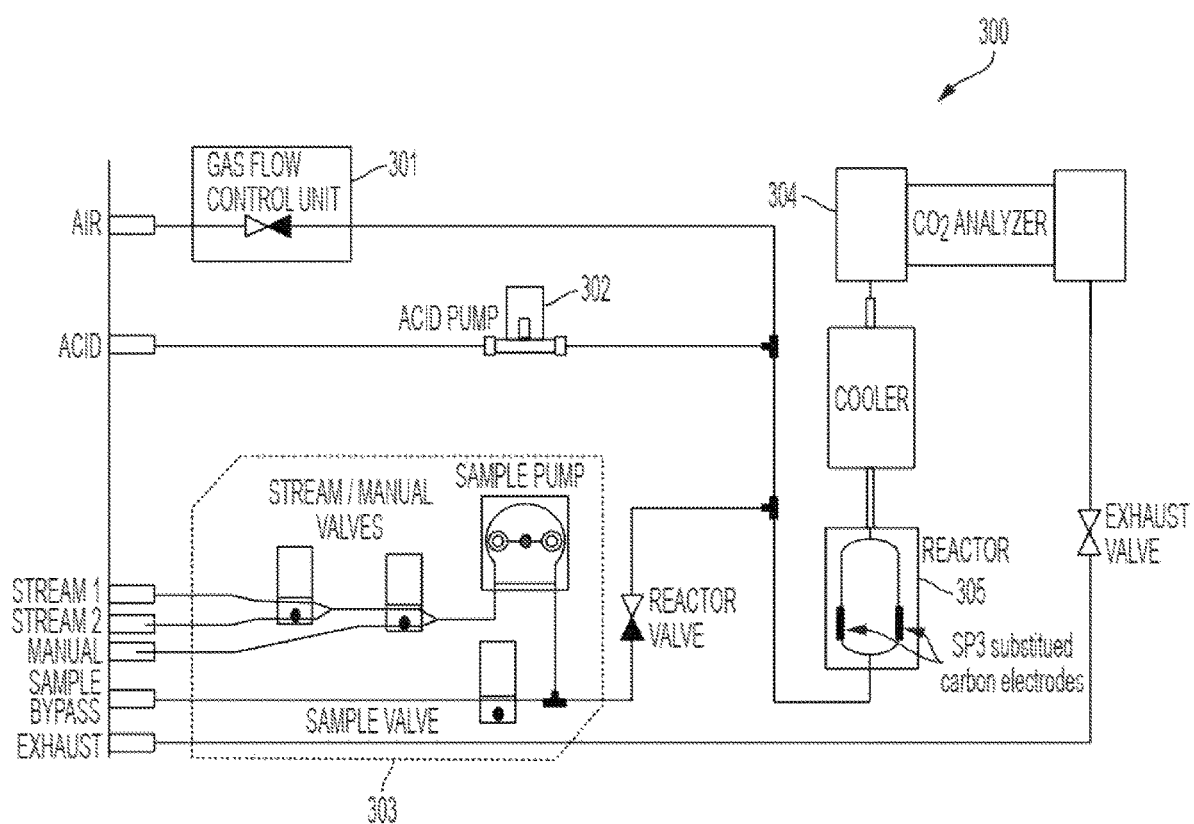
FIG. 3 illustrates an example SP3 substituted carbon electrode TOC analyzer according to an embodiment.

Using the system as described herein and illustrated in FIG. 3, the conventional analyzer system can be simplified. For example, an example embodiment of the system 300 as described herein can use air as the sparge gas, rather than oxygen. Accordingly, the oxygen module 201 can be removed and replaced with a gas flow control unit 301. Not only does this remove the large oxygen module 201, but it also reduces the amount of air that is required to generate the required oxygen of the conventional system. Additionally, only a single reagent is needed in the system 300 as described herein. Thus, one of the reagent pumps 202 and/or 203 can be removed from the system 300 (e.g., in FIG. 3 only the acid reagent pump 302 is present). The sample electronics 203 can also be simplified. The mixer portion of the reactor 206 can be removed and replaced with the SP3 substituted solid carbon electrodes 305 as described herein. Additionally, the system 300 as described herein does not require ozone. Therefore, both the large ozone generator 205 and the ozone destructor 208 can be removed. The system 300 as described herein may also result in a simpler $CO_2$ analyzer 207, which is shown as 304 in FIG. 3. Additionally, the system requires fewer and smaller components which results in a smaller overall housing.

Figure 4:
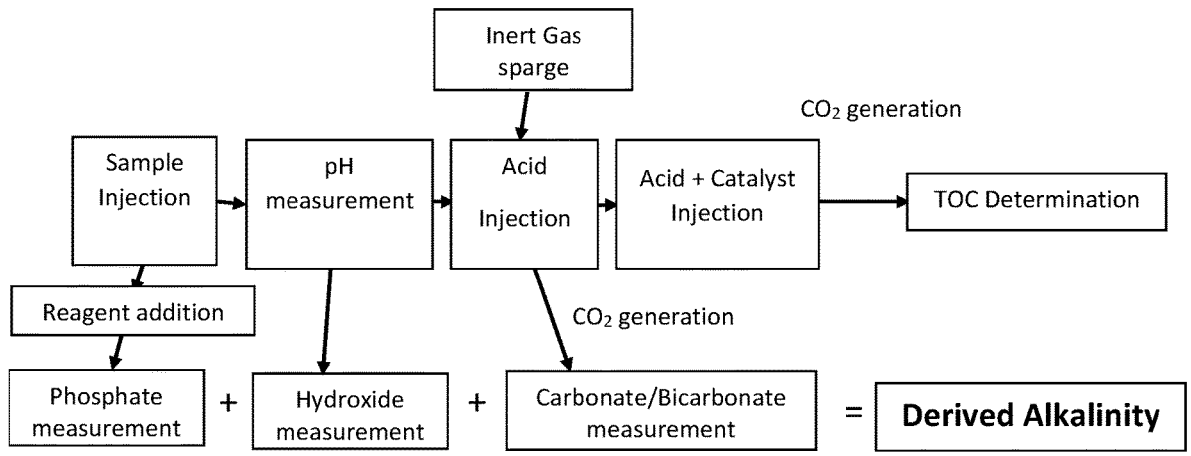
FIG. 4 illustrates an example flow chart of a derived alkalinity method and system.

Referring now to FIG. 4, an example flow chart of derived alkalinity method and system is illustrated. As described in detail above, a fluid sample may be injected into the device. A regent or colorimetric reagent may be added and phosphate measured using a colorimetric method. In an embodiment, a pH may be measured of the fluid sample and an amount of hydroxide measured of the fluid sample. In an embodiment, an acid may convert all the inorganic carbon to carbon dioxide. The carbon dioxide may be measured to determine a carbonate and/or bicarbonate measurement present in the fluid sample before oxidation of the fluid sample. In an embodiment, a gas may be used to sparge the fluid sample at the acid injection step. In an embodiment, an acid and catalyst may be injected into the fluid sample. In an embodiment, a TOC of the fluid sample may be determined. In an embodiment, the phosphate measurement, hydroxide measurement, and carbonate/bicarbonate generated from the inorganic carbon measurement may be used to determine a derived alkalinity (FIG. 1, step 108).

Figure 5:
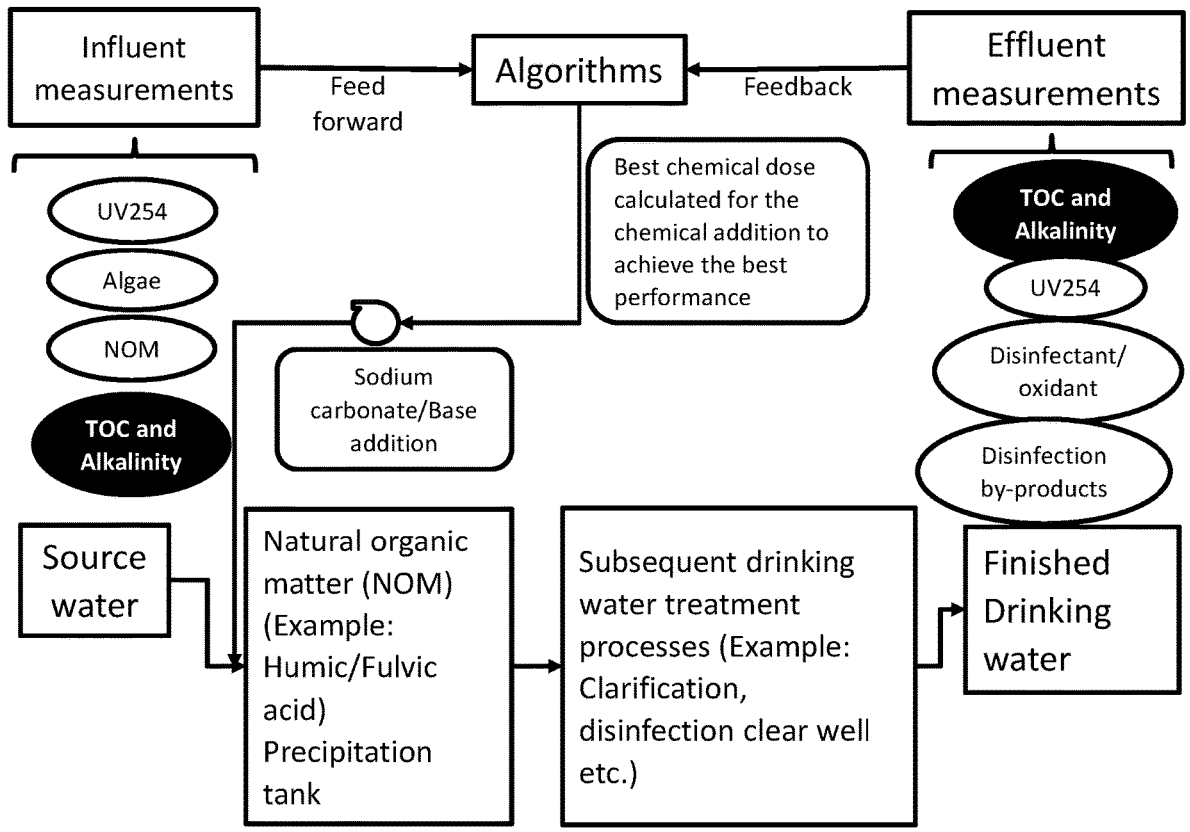
FIG. 5 illustrates an example feed forward and feedback of a fluid sample using influent and effluent measurements.

Referring now to FIG. 5, an example feed forward and feedback using methods described herein is illustrated. In an embodiment, the device and method may use alkalinity, TOC, and other measurements to monitor water quality at an influent and effluent location. The device and method may determine the degree of disinfection chemical/reagents given a volume of water to be treated such that disinfection by-products are kept to a minimum or below desired or regulatory levels. In an embodiment, the device may measure influent and/or effluent characteristics. For example, influent measurements may include UV254, algae, natural organic matter (NOM), TOC and alkalinity measurements. The influent measurements may provide a feed forward input for the system. For example, effluent measurements may include UV254, disinfectant/oxidant, disinfection by-products, TOC and alkalinity measurements. The effluent measurements may provide a feedback input for the system.

In an embodiment, the influent and effluent characteristics, may be used to determine the chemical dose for precipitation of organic precursors, or the like, to maintain a quality of water required by a facility. In an embodiment, the influent and effluent characteristics may be used to determine a proper amount of treatment reagents such as sodium carbonate, base addition, other, or the like to the fluid sample. In an embodiment, the method or device may add the treatment reagents to a water source. The addition of the treatment reagents may precede or coincide with a step of treatment such as the precipitation tank, and prior to subsequent water treatment such as clarification, disinfection, or the like.

In an embodiment, the method may measure alkalinity and TOC simultaneously to enable the reduction of the DBP formation. For example, if the alkalinity is low and organics are high then there is a high propensity for DBP formation. Quantities of chemicals required may be calculated based on the alkalinity and TOC concentrations determined by the system and method to prevent the DBP formation.

In an embodiment, alkalinity levels may be optimized in real time by online monitoring and on-demand chemical addition to minimize the formation of DBP's. This simultaneous measurement of alkalinity and TOC achieved by the system and method may generate the buffer capacity and organic precursor concentration which will may be used in a feedback loop to optimize the chemical addition in real time that would result in cost and chemical savings while achieve efficient reduction of DBP formation. This real time control (RTC) may serve as a proactive tool to minimize the DBP formation.

In an embodiment, the simultaneous measurements of TOC and alkalinity in one system at the influent and effluent provides the ability to calculate the percent reduction of organics and the relational dependence on the delta alkalinity is obtained. The efficiency of the precipitation process due the chemical addition is achieved in real time from these calculations. Dynamic real time chemical dose control may be implemented to achieve the highest efficiency of precipitation The DBP measurement at the effluent may provide alarms, thresholds, ranges, or the like if the level violates the regulatory limit. Chemical treatment processes that are performed upstream are managed automatically or manually to bring the DBP level below the required regulatory, desired, or required limit. This event monitoring feature may be enabled by a system that can measure the TOC and alkalinity simultaneously.

The various embodiments described herein thus represent a technical improvement to conventional total organic carbon measuring techniques. Using the techniques described herein, an embodiment may receive a fluid sample containing organic carbon and oxidize the sample to produce the oxidation products carbonate and oxalate. An embodiment may then introduce an acid reagent and a metallic catalyst to the sample to convert the carbonate and oxalate to carbon dioxide, which can then be measured. Such techniques provide a more accurate way of measuring the total organic carbon content in a sample and provide a more cost-effective approach over existing methods.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for deriving an alkalinity measurement, comprising:
   introducing, in a reaction chamber of an analyzer, a fluid sample comprising inorganic carbon, wherein the reaction chamber includes an electrochemical cell and wherein the electrochemical cell comprises an SP3 substituted carbon electrode doped with a conductivity elevating composition;
   measuring, using a phosphate analyzer of the analyzer, a phosphate amount of the fluid sample using a colorimetric reagent;
   measuring, using a pH sensor of the analyzer, a pH of the fluid sample, wherein the pH of the fluid sample correlates to a hydroxide amount of the fluid sample;
   introducing an acid reagent to convert the inorganic carbon to an amount of carbon dioxide, wherein the inorganic carbon comprises carbonate and bicarbonate;
   applying, using a generator of the analyzer, a positive potential to the SP3 substituted carbon electrode, the positive potential being sufficient to oxidize organics in the fluid sample to produce carbonate and partially oxidized organics;
   introducing, during the application of the positive potential to the SP3 substituted carbon electrode and in the reaction chamber, the acid reagent converting the carbonate and the partially oxidized organics to another amount of carbon dioxide;

determining total organic carbon by detecting, using a metallic catalyst in the presence of the acid reagent and at least one detector of the analyzer, the another amount of carbon dioxide produced by the oxidation; and determining a derived alkalinity based upon the phosphate amount, the hydroxide amount, and the amount of carbon dioxide generated from the inorganic carbon, wherein the determining total organic carbon and determining the derived alkalinity occur simultaneously from the fluid sample in the same reaction chamber.

2. The method of claim 1, wherein the introducing the acid reagent further comprises sparging with an inert gas.

3. The method of claim 2, wherein the inert gas comprises nitrogen.

4. The method of claim 1, further comprising measuring an initial pH of the fluid sample and purging the fluid sample with an inert gas directly thereafter.

5. The method of claim 1, further comprising measuring an influent characteristic upstream of the analyzer and an effluent characteristic downstream of the analyzer.

6. The method of claim 5, wherein the influent characteristic is selected from the group consisting of: alkalinity and total organic carbon.

7. The method of claim 5, wherein the effluent characteristic is selected from the group consisting of: alkalinity and total organic carbon.

8. The method of claim 5, further comprising determining a concentration of required disinfection chemical based at least in part upon the influent characteristic and the effluent characteristic.

9. The method of claim 1, further comprising calculating a formation of disinfection by-products based at least in part upon the derived alkalinity and the total organic carbon.

10. The method of claim 1, wherein the reaction chamber of the analyzer comprises a stopped-flow design for the fluid sample.

* * * * *